United States Patent
Hildebrand et al.

(10) Patent No.: US 7,684,598 B2
(45) Date of Patent: Mar. 23, 2010

(54) METHOD AND APPARATUS FOR THE LOADING AND POSTPROCESSING OF DIGITAL THREE-DIMENSIONAL DATA

(75) Inventors: Thomas Hildebrand, Moehrendorf (DE); Marc Rose, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1108 days.

(21) Appl. No.: 11/182,188

(22) Filed: Jul. 15, 2005

(65) Prior Publication Data
US 2006/0280349 A1    Dec. 14, 2006

Related U.S. Application Data

(60) Provisional application No. 60/588,369, filed on Jul. 16, 2004.

(30) Foreign Application Priority Data
Jul. 16, 2004    (DE) .................. 10 2004 034 503

(51) Int. Cl.
  *G06K 9/00* (2006.01)
  *G06K 9/36* (2006.01)
(52) U.S. Cl. ...................... 382/128; 382/276
(58) Field of Classification Search ......... 382/128–132, 382/276; 345/419, 428, 429, 430, 582
See application file for complete search history.

(56) References Cited

U.S. PATENT DOCUMENTS

| 5,313,567 | A | 5/1994 | Civanlar et al. |
| 6,184,888 | B1 * | 2/2001 | Yuasa et al. .................. 345/419 |
| 6,522,336 | B1 * | 2/2003 | Yuasa .......................... 345/582 |
| 6,656,279 | B2 | 12/2003 | Seifert |
| 7,272,251 | B2 * | 9/2007 | Acar et al. ................... 382/128 |
| 7,333,648 | B2 * | 2/2008 | Edic et al. ................... 382/131 |
| 7,415,147 | B2 * | 8/2008 | Ying et al. .................. 382/132 |
| 7,447,343 | B2 * | 11/2008 | Barfuss et al. .............. 382/128 |

FOREIGN PATENT DOCUMENTS

| CN | 1278350 | 12/2000 |
| WO | WO 9923610 | 5/1999 |

* cited by examiner

*Primary Examiner*—Yon Couso
(74) *Attorney, Agent, or Firm*—Harness, Dickey & Pierce, P.L.C.

(57) ABSTRACT

A method and an apparatus are for the loading and postprocessing of three-dimensional digital volume data, in particular from the medical field. Layer images are usually acquired by CT or MR devices and combined to form a volume data record. These combined data are fed to one or more postprocessing methods, such as e.g. the VRT, MIP and/or MPR technique. These postprocessing methods can already be used for a portion of the loaded data directly after the beginning of the loading operation.

24 Claims, 1 Drawing Sheet

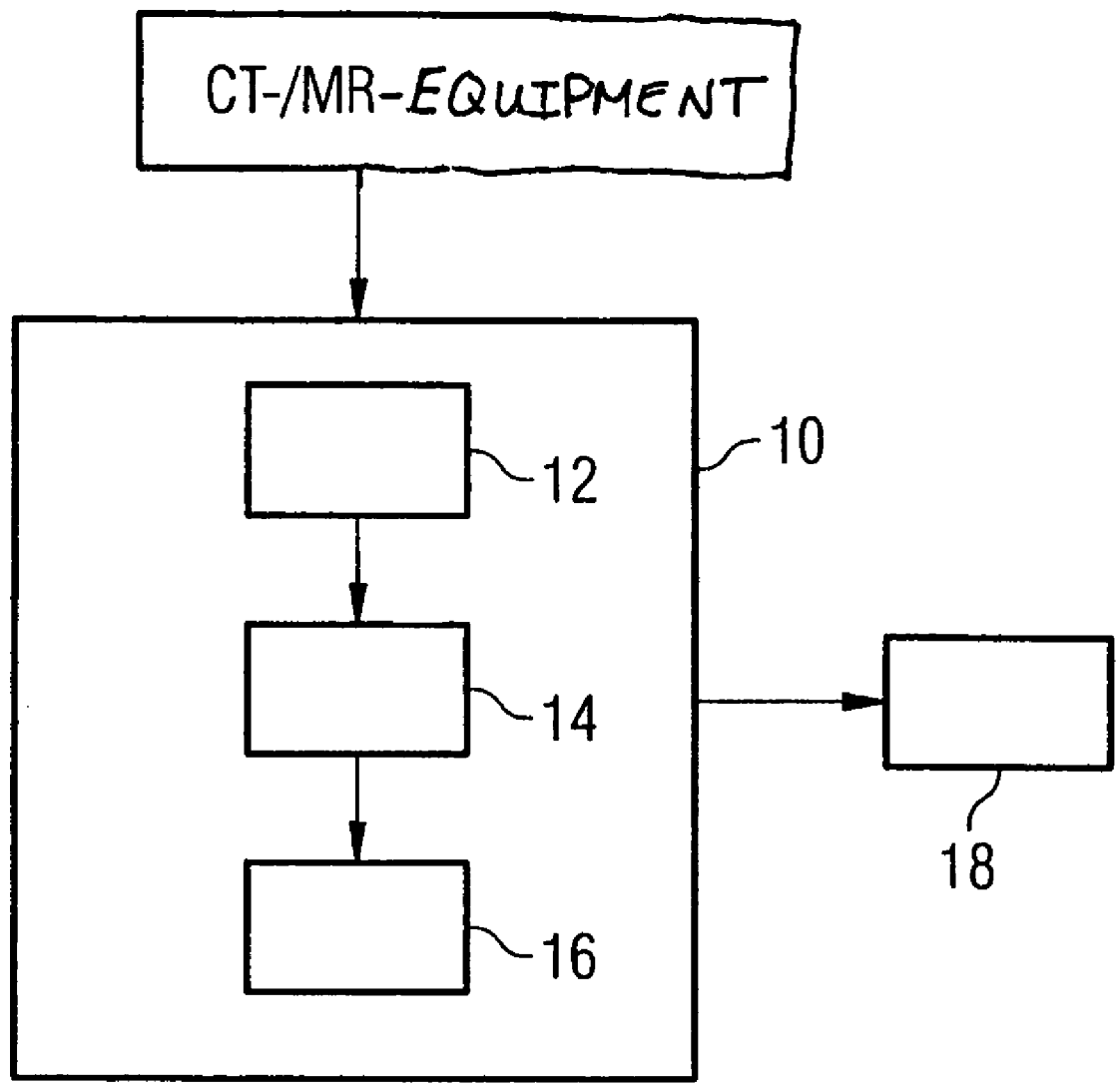

METHOD AND APPARATUS FOR THE LOADING AND POSTPROCESSING OF DIGITAL THREE-DIMENSIONAL DATA

The present application hereby claims priority under 35 U.S.C. §119 on German patent application number DE 10 2004 034 503.1 filed Jul. 16, 2004, and on U.S. provisional patent application Ser. No. 60/588,369 filed Jul. 16, 2004, the entire contents of each which are hereby incorporated herein by reference.

FIELD

The invention is generally related to the field of image processing and may relate, in particular, to a method and/or an apparatus for the postprocessing of three-dimensional image data. Even more particularly, it may relate to the medical field for the purpose of establishing a finding.

BACKGROUND

In clinical practice, various types of image data are acquired from a patient and, if appropriate, processed further at a later point in time for the purpose of creating a finding or establishing a finding by a physician. These may be, inter alia, images that have been acquired by a computer tomograph, by an ultrasound device or by a nuclear spin device for example.

In image processing in the medical sector, large volumes of data have to be processed in order for an image, that can be further used, to be displayed. However, the procedure according to the invention can be used not only in the medical field but also in arbitrary other fields of application which are based on a postprocessing of image data.

In order that the acquired layer image data can be represented on a display device, they have to be transferred or converted—proceeding from their original two-dimensional form that is prescribed by the acquisition device—into a 3D representation form, so that a volume representation is possible on the display device. For this purpose, the collected layer images are computationally placed one above the other. The 3D representation thus obtained is then fed to further post processing methods.

These postprocessing methods for three-dimensional image data relate e.g. to contrasting the represented pixels in relation to one other or to the possibility of being able to adopt other observer perspectives for the respective object. Thus, it may be necessary, by way of example, to have not only the plan view of the lung but also a front view or to have displayed a section through a specific axis. The type of selected or applied postprocessing method(s) is defined in the application case and, in particular, by the treating physician.

Furthermore, the image data are often subjected to an application-case-specific representation method. Thus, the user may set or define so-called transfer functions that stipulate, for example, that specific structures are to be represented and others are not to be represented because they are not relevant in this case. Another setting that can be effected is that specific types of tissue are not to be represented as opaque, in order that the underlying layers are likewise visible. Thus, specific settings that are relevant to the representation of the image are made depending on the application case.

In the systems known from the prior art, all of the image data are first finally processed or converted before the postprocessing methods can be used. The previous procedure according to the prior art leads to the disadvantage that the user is exposed to high waiting times which—e.g. in an acute case—are unacceptable. A further disadvantageous effect lies in the fact that the user is also not informed about the current stage of calculation and is therefore compelled to wait for an unforeseeable time interval until the construction of the image is complete.

Scanners of CT and MR devices usually generate layer images which are then converted so that they image a three-dimensional volume. This three-dimensional image is then fed to further postprocessing methods, if appropriate.

In the known methods, a postprocessing method could only be employed after the volume data were completely loaded. In these known methods, it was very problematic that the user was repeatedly exposed to long waiting times. He therefore had to wait until the data had been completely loaded and only then could he use postprocessing methods, for the results of which he had to wait in some instances even longer and thus repeatedly.

In some medical applications, in particular, it may on the other hand have even been expedient and sufficient to prematurely interrupt an image construction process if e.g. at this point in time it was already foreseeable that only an image excerpt was of interest for the current issue in question.

A further known approach relates to the procedure of repeatedly calculating the three-dimensional images from the portion of the volume that has been loaded up to this point in time. However, the overall duration of the loading operation is lengthened considerably as a result of this.

SUMMARY

Therefore, a method is desirable which enables the postprocessing methods to be employed already prior to the complete image construction.

Therefore, an embodiment of the present invention has an object of demonstrating a way of making it possible to reduce or even minimize waiting times which arise on account of an operation of loading three-dimensional image data and/or on account of a postprocessing operation. A particular aspect may in this case lie in emphasizing the clinical relevance, i.e. diagnostically valuable information is intended to be available early on.

An object of at least one embodiment may be achieved by a method for the processing and/or postprocessing of image data, in particular of three-dimensional digital image data, comprising:

loading the image data for representation on a display device and postprocessing the image data, the steps of loading and postprocessing being temporally interlaced, wherein the postprocessing of the image data can already be effected on a loaded portion of the image data directly after the beginning of loading.

Furthermore, an object of at least one embodiment may be achieved by an apparatus for the processing and/or postprocessing of image data, in particular of three-dimensional digital image data, comprising:

at least one loading module, which is designed for loading the image data for representation on a display device, and at least one postprocessing module, which is designed for the postprocessing of the image data, the loading module and the postprocessing module operating in temporally interlaced fashion, wherein at least one loaded portion of the image data can already be fed to the postprocessing module for postprocessing directly after the beginning of a loading operation of the loading module.

According to at least one embodiment of the invention, the point in time at which the postprocessing of the image data can begin is independent of the execution or completion of the loading operation. Thus, at least the loaded portion of the image data can be postprocessed at an arbitrary point in time.

The time interval for the beginning of the postprocessing operation may be in at least one embodiment defined between: directly after the beginning of a loading operation and before the conclusion of the complete loading operation. In this case, the user has a possibility of influence according to at least one embodiment of the invention in that he can determine this point in time from application case to application case.

In one advantageous embodiment of the invention, the user can set the image resolution that he desires. Thus, in urgent cases requiring only a rough view of an organ, it may be expedient to set a lower image resolution in order that the waiting times, on account of the calculation of the image data, can be reduced. In this connection, one advantage of the method presented here resides in the fact that, at least for the loaded portion of the image data, an increased or even maximum, or a desired image resolution—depending on the user's setting—is even already available directly after the beginning of loading. This increases the quality of the result overall.

The image data are usually postprocessed on the display device itself. However, in the case of complex clinical structures, it is also possible for the image data to be acquired on one device, calculated on another device—depending on the chosen settings of the user—and, if appropriate, displayed on a further device. In this case, all the devices are in data interchange with one another.

There are various mechanisms for the postprocessing of three-dimensional image data. In at least one embodiment of the invention, in principle, all postprocessing mechanisms can be used. Preferably, however, recourse is had to at least one of the following mechanisms in the context of postprocessing:

VRT or volume rendering technique,
MIP or maximum intensity projection, and
MPR or multiplanar reconstruction (multiplanar reformatting).

The VRT technique is a relatively complicated and complex image postprocessing method. All detected anatomical body structures (e.g. cervical spinal column and adjoining arteries) are assigned different transparency levels or opacity values, degrees of brightness and colors. This assignment is one-to-one in the case of CT data and is based on a normalized scale, the so-called Houndsfield unit scale. With this technique, semitransparent and nontransparent VRT objects can be represented simultaneously and enable the user to have a rapid overview of the anatomical structures in question. Thus, in the above example, the artery can be represented and displayed by means of the cervical spinal column lying in front of it being represented in transparent fashion.

The MIP method is a visualization method geared to the fact that only an excerpt from the data or a partial volume is relevant, which is represented as far as possible in differentiated fashion. Thus, the user firstly chooses a volume of interest (VOI). The three-dimensional impression of this volume is generated in this technique by the fact that, from a given viewing direction, only in each case the 3D volume points with increased or even maximum or respectively decreased or even minimum grey-scale values are projected into a two-dimensional image.

The MPR principle makes it possible to view an imaged organ or an anatomical structure from arbitrary perspectives. Consequently, the volume object or the organ can also be viewed from a different perspective than the acquisition plane. For this purpose, the user defines a desired sectional plane, e.g. a sagittal, coronary, paraaxial or some other section. The corresponding images are calculated by means of this technique—without the patient being additionally exposed to radiation.

In an alternative embodiment, still other postprocessing methods, such as e.g. surface reconstruction (shaded surface display, SSD), are likewise used in order to postprocess the original data for easier visualization. Embodiments of the invention are not restricted to one principle of postprocessing, but rather can apply to arbitrary methods of postprocessing for example.

All postprocessing methods that can be used have the disadvantage, however, that they require an immense demand for computing power which can take up very much time on a customary workstation. Therefore, the acceptance of these thoroughly important and quality-increasing methods has hitherto been low in the clinical environment.

According to an embodiment of the invention, the total waiting time that results on account of the loading time of the three-dimensional image data is subdivided into a plurality of blocks of waiting times, which has the effect that the user can already obtain at least a partial result at an earlier point in time. This is achieved in that portions or volume data excerpts can already be postprocessed directly after the loading operation for the corresponding data.

In one advantageous embodiment, it is provided that the image data can be postprocessed in different resolution levels. The choice of the resolution level in turn has an influence on the resulting waiting time.

The image data usually have to be postprocessed. However, it is also possible for the method only to load and represent the image data without a postprocessing being effected. The initial original data can thus be used for the further processing or establishing a finding. A postprocessing is not mandatory, merely optional.

The method is preferably desired such that further processing mechanisms and/or applications can be applied to the already loaded portion of the image data, in particular a size alteration, a contrast alteration or a changing of the transfer function. The original data can thus be fed to postprocessing methods and/or further processing applications directly after the beginning of the loading operation.

In an alternative embodiment, the method additionally comprises the following step of:

acquiring the image data and/or data records necessary for a calculation. This method step advantageously temporally precedes the loading and postprocessing phase. However, it is also conceivable for this step to be temporally intertwined with the respective other steps, or to be configured such that it overlaps them, so that in each case only a portion of the data is acquired and fed to the other method steps and the partial results are subsequently combined again.

The acquisition of the image data usually includes identifying at least one corresponding data record, reading in or transferring the data record, e.g. from a device to a display device.

The above-described method embodiments according to the invention may also be designed as a computer program product, with a computer-readable medium and with a computer program, in the case of which the computer is caused to carry out the above-described method according to at least one embodiment of the invention after the computer program has been loaded.

An alternative solution for achieving the object provides a storage medium which is intended for storing the computer-implemented method described above and is computer-readable.

Layer image data records may be acquired via tomograms or magnetic resonance tomograms. PET images or images from angiography may also be the basis of the method according to at least one embodiment of the invention.

BRIEF DESCRIPTION OF THE DRAWINGS

In the detailed description of the figure below, exemplary embodiments with their features and further advantages which are not to be understood as restrictive are discussed with reference to the drawings, in which:

FIG. 1 shows a schematic illustration of components of an apparatus according to the invention in accordance with an advantageous embodiment of the invention.

DETAILED DESCRIPTION OF THE EXAMPLE EMBODIMENTS

At least one embodiment of the invention relates to a method and/or an apparatus—designated generally by 10—for the electronic processing, postprocessing and/or representation of three-dimensional images, in particular of layer image recordings in the medical field.

In a first step, layer image data records are acquired. This is usually done by means of tomograms or magnetic resonance tomograms. However, PET data records, ultrasound recordings or images from rotation angiography may also form the basis of the method or apparatus according to at least one embodiment of the invention.

The apparatus 10 usually includes an acquisition module 12, which is designed for the acquisition, provision, transfer and/or selection of the relevant data records. The acquisition module 12 is in data interchange with the recording devices or with devices that store the acquired data records, such as e.g. a CT device.

A loading module 14 is intended for the loading and/or for the calculation of the volume data. It is in a data interchange with the acquisition module 12 and a postprocessing module 16.

However, it is also possible for no acquisition module 12 to be provided; in this case, the loading module 14 is in data interchange with the recording devices. As an alternative, it is possible for no loading module 14 to be provided; the acquisition module 12 is then in data interchange with the devices, on the one hand, and with the postprocessing module 16, on the other hand, and also serves for calculating the volume data records from the original data.

In principle in at least one embodiment, it is always necessary to provide at least one module that is intended for the transformation of the sectional images into a three-dimensional view. For this purpose, the original data records assigned to the diverse sectional images have to be converted or calculated according to suitable mechanisms. The two-dimensional sectional images are stacked one above the other in computer-aided fashion. In this case, in addition to the stacking order, it is also necessary to take account of a matching zoom factor and excerpt (field of view).

The apparatus 10 or the postprocessing module 16 forward the postprocessed data to a display device 18 for representation.

Since every recording of layer images is associated with an expenditure (on the one hand for the patient and on the other hand also from a temporal point of view) and it is often necessary from medical standpoints, however, to have not only a three-dimensional representation but also a different perspective and/or a different viewing plane of the same organ or of the same patient, methods are used which permit a data postprocessing and a different representation of three-dimensional image data records once they have been acquired, without necessitating new recordings.

In alternative embodiments of the invention, it is provided that the acquisition module 12, the loading module 14 or the postprocessing module 16 is not arranged within the apparatus 10, but rather in each case as an external element.

If there is a clearly defined and demarcated interest e.g. only in an excerpt from volume data in a specific perspective, then according to at least one embodiment of the invention the user can already instigate a postprocessing method directly after the beginning of the loading operation for the entire volume data, which postprocessing method is applied to the hitherto loaded portion of the volume data. A VRT, MIP or MPR technique, inter alia, may be used here.

If no postprocessing is desired, then this can be set as well; the original data records are then fed to the display device 18.

Usually, however, a postprocessing is to be effected for the data in order to facilitate the temporally succeeding finding by a physician. According to at least one embodiment of the invention, the original images are used for the 3D postprocessing during loading: as soon as a small portion of the layer images has been loaded, the latter are fed to an arbitrary 3D postprocessing method or to the postprocessing module 16. The user may optionally have recourse to further mechanisms in the image representation of the at least partially loaded data, such as e.g. scrolling back and forth between different views or pages, changing the contrast or setting a zoom factor which reduces or magnifies the represented image.

One advantage of at least one embodiment of the present invention resides in the fact that—in comparison with the methods according to the prior art—the finding can be begun substantially earlier since the physician, e.g. in radiological diagnosis, never studies all of the volume data all at once, but rather can always attend only to an excerpt in each case and works forward progressively as it were proceeding from one end.

A further advantage is to be seen in the fact that directly after the beginning of the loading operation, the maximum image resolution is available for the loaded portion of the data.

In at least one embodiment, the interface to the postprocessing methods is configured differently according to at least one embodiment of the invention by virtue of the fact that these no longer require all of the volume data to be communicated. Rather, it suffices for the latter to be communicated to the postprocessing module 16 step by step or in a plurality of blocks. As soon as one block of volume data has been calculated or loaded, it can already be passed on to the postprocessing module 16. Thus, an incremental postprocessing results and, furthermore, the postprocessing is already executed before the complete loading operation.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for at least one of processing and postprocessing of medical image volume data, comprising:
    loading, using a processor, the medical image volume data for representation on a display device, where the loading is executed in portions of the medical image volume data; and
    postprocessing the medical image volume data, using the processor, where the loading and the postprocessing is temporally interlaced, so that the postprocessing of the medical image volume data is executable on a loaded portion of the medical image volume data directly after beginning the loading.

2. The method as claimed in claim 1, wherein at least the loaded portion of the medical image volume data is postprocessable at a selectable point in time that lies directly after the beginning of the loading and before the loading is completed, such that the loading is completed when all the portions of the medical image volume data are loaded.

3. The method as claimed in claim 1, wherein at least for the loaded portion of the medical image volume data, at least one of a maximum and a desired image resolution is already available directly after the beginning of the loading.

4. The method as claimed in claim 1, wherein the postprocessing is based on at least one of a volume rendering technique, at least one of a maximum and minimum intensity projection, a multiplanar reconstruction and other mechanisms for the postprocessing of medical image volume data.

5. The method as claimed in claim 1, wherein the medical image volume data are postprocessed at different resolution levels.

6. The method as claimed in claim 1, wherein at least one of further processing mechanisms and applications are applicable to the already loaded portion of medical image volume data.

7. The method as claimed in claim 1, further comprising:
    acquiring the medical image volume data necessary for a calculation.

8. The method as claimed in claim 7, wherein the acquiring includes identifying at least one corresponding data record, and at least one of reading in and transferring the at least one corresponding data record.

9. An apparatus for at least one of the processing and postprocessing of medical image volume data, comprising:
    at least one loading module, designed to load the medical image volume data for representation on a display device, where the loading module loads in portions of the medical image volume data; and
    at least one postprocessing module, designed to postprocess the medical image volume data, where the at least one loading module and the at least one postprocessing module operate in temporally interlaced fashion, so that at least one loaded portion of the medical image volume data is feedable to the postprocessing module for postprocessing directly after beginning a loading operation of the loading module.

10. The apparatus as claimed in claim 9, wherein the at least one loaded portion of the medical image volume data is postprocessable at a selectable point in time that lies directly after the beginning of the loading operation and before the loading operation is completed, such that the loading operation is completed when all the portions of the medical image volume data are loaded by the loading module.

11. The apparatus as claimed in claim 9, wherein at least for the loaded portion of the medical image volume data, at least one of a maximum and a desired image resolution is already available directly after beginning the loading.

12. The apparatus as claimed in claim 9, wherein the postprocessing of the medical image volume data is effected on at least one of the display device and a device that is in data interchange with the display device.

13. The apparatus as claimed in claim 9, wherein the postprocessing is based on at least one a volume rendering technique, at least one of a maximum and minimum intensity projection, and a multiplanar reconstruction.

14. The apparatus as claimed in claim 9, wherein the medical image volume data are postprocessed at different resolution levels.

15. The apparatus as claimed in claim 9, wherein at least one of further processing mechanisms and applications are applicable to the already loaded portion of medical image volume data.

16. The apparatus as claimed in claim 9, further comprising:
    at least one acquisition module, designed to acquire the medical image volume data.

17. The apparatus as claimed in claim 16, wherein the at least one acquisition module is designed to identify at least one corresponding data record, for at least one of reading in and transferring the data record.

18. The method as claimed in claim 1, wherein the medical image volume data includes three-dimensional digital medical image volume data.

19. The method as claimed in claim 2, wherein at least for the loaded portion of the medical image volume data, at least one of a maximum and a desired image resolution is already available directly after the beginning of the loading.

20. The method as claimed in claim 6, wherein the at least one of further processing mechanisms and applications include at least one of a size alteration, a contrast alteration and a change between image parts.

21. The apparatus as claimed in claim 9, wherein the medical image volume data includes three-dimensional digital medical image volume data.

22. The apparatus as claimed in claim 10, wherein at least for the loaded portion of the medical image volume data, at least one of a maximum and a desired image resolution is already available directly after beginning the loading.

23. The apparatus as claimed in claim 15, wherein the at least one of further processing mechanisms and applications include at least one of a size alteration, a contrast alteration and a change between image parts.

24. A computer-readable medium storing a computer program for at least one of processing and postprocessing of medical image volume data, which when executed on a computer, cause the computer to execute instructions comprising:
  loading the medical image volume data for representation on a display device, where the loading is executed in portions of the medical image volume data; and
  postprocessing the medical image volume data, where the loading and the postprocessing is temporally interlaced, so that the postprocessing of the medical image volume data is executable on a loaded portion of the medical image volume data directly after beginning the loading.

* * * * *